Figure 1:
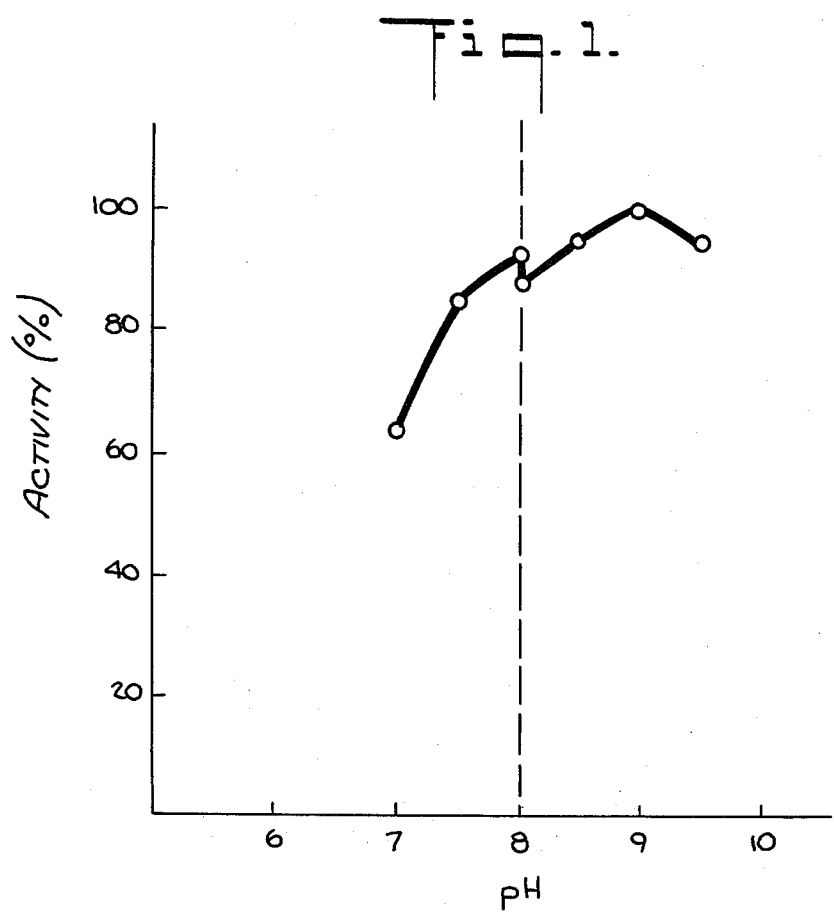

United States Patent [19]

Kimura et al.

[11] 4,391,910

[45] Jul. 5, 1983

[54] PROCESSES FOR PRODUCING THERMOPHILIC ASPARTASE

[75] Inventors: Kazuo Kimura, Hofu; Kenichiro Takayama, Atsugi; Yutaka Ado, Machida; Tamotsu Kawamoto, Sagamihara; Izumi Masunaga, Fuchu, all of Japan

[73] Assignee: Kyowa Hakko Kogyo Co., Ltd., Tokyo, Japan

[21] Appl. No.: 209,494

[22] Filed: Nov. 24, 1980

[30] Foreign Application Priority Data

Nov. 27, 1979 [JP] Japan .............................. 54-152468

[51] Int. Cl.³ .................... C12N 9/88; C12P 13/20; C12R 1/07
[52] U.S. Cl. ................................. 435/232; 435/109; 435/832
[58] Field of Search ............... 435/109, 232, 832, 833, 435/836, 839

[56] References Cited

U.S. PATENT DOCUMENTS

| | | | |
|---|---|---|---|
| 3,198,712 | 8/1965 | Takahashi et al. ................. | 435/109 |
| 3,791,926 | 2/1974 | Chibata et al. ..................... | 435/109 |
| 3,933,586 | 1/1976 | Duc .................................... | 435/109 |

FOREIGN PATENT DOCUMENTS 38-6588  5/1963  Japan .
880234  10/1961  United Kingdom .

OTHER PUBLICATIONS

*Bergey's Manual of Determinative Bacteriology,* 8th Ed., Buchanan, Ed. 1973, Williams and Wilkins Co., Baltimore, pp. 531–541.
*The American Type Culture Collection Catalogue of Strains* I, 12th Ed., American Type Culture Collection, Rockville, Md., 1976, pp. 25, 27, 28, 31.
Suzuki et al., Production of L-Arpartic Acid from Fumaric Acid by a Fumaric Acid-Assimilating Obligate Thermophile, Bacillus Stearothermophikis, KP104/EP, J. Appl. Microbiology, Biotechnol., vol. 11, 1980, pp. 23–27.
Samejima et al., Enzyme Engineering, vol. 2, pp. 131–135.
Chibata et al., App. Mic., vol. 27, pp. 878–885.
Chem. Abst., vol. 90, 1979, No. 164405v.
Chem. Abst., vol. 86, 1977, No. 167625v.
Chem. Abst., vol. 81, 1974, No. 89797h.
Chem. Abst., vol. 74, 1971, No. 84421b.
Chem. Abst., vol. 66, 1967, No. 542682z.
Chem. Abst., vol. 55, 1981, No. 19131a.
Chem. Abst., vol. 70, 1969, No. 64530a.
Chem. Abst., vol. 51, 1957, No. 9738g.
Chem. Abst., vol. 48, 1954, No. 5288a.

*Primary Examiner*—Thomas G. Wiseman
*Assistant Examiner*—Kathleen S. McCowin
*Attorney, Agent, or Firm*—Fitzpatrick, Cella, Harper & Scinto

[57] ABSTRACT

Thermophilic aspartase is produced by culturing a microorganism belonging to the genus Bacillus. The enzyme is useful as a catalyst in the production of L-aspartic acid from ammonium fumarate or a mixture of fumaric acid and ammonia.

4 Claims, 4 Drawing Figures

PROCESSES FOR PRODUCING THERMOPHILIC ASPARTASE

BACKGROUND OF THE INVENTION

The present invention relates generally to a novel thermophilic aspartase, a process for the production thereof, microorganisms capable of producing the enzyme and a process for producing L-aspartic acid using the enzyme.

L-aspartic acid is an important amino acid and is useful as a drug for recuperation from fatigue, an antidote against ammonia, a food additive or a diagnostic agent.

Heretofore, L-aspartic acid has been commercially produced by fermenting a microorganism such as *Escherichia coli* (Japanese Patent Publication No. 6588/63). Additional methods for the production of L-aspartic acid using immobilized cells have also been reported [Samejima and Kimura: Enzyme Engineering 2 131, Plenum Press, New York and London, (1974), Tosa and Chibata: Applied Microbiology Vol. 27, 886, (1974)].

While the aforementioned methods provide commercially acceptable yields of the product, it would be advantageous in the prevention of contamination, acceleration of enzymatic reaction, saving of energy and the like to carry out the fermentation procedures, enzymatic reactions, etc. at a high temperature.

To this end, after studying the aspartase activity of various thermophilic bacteria it has now been found that thermophilic bacteria of the genus Bacillus produce thermophilic aspartase which can readily be used for the production of L-aspartic acid in a high temperature environment.

SUMMARY OF THE INVENTION

In accordance with the present invention, thermophilic aspartase is produced by culturing a microorganism belonging to the genus Bacillus which is capable of producing the enzyme in a nutrient medium, accumulating the enzyme in the culture liquor and recovering the same therefrom.

According to a further aspect of the invention, L-aspartic acid is produced by enzymatic reaction of ammonium fumarate or a mixture of fumaric acid and ammonia using thermophilic aspartase and thereafter recovering L-aspartic acid from the reaction mixture.

DESCRIPTION OF THE INVENTION

Thermophilic aspartase is produced, according to the invention, by culturing a microorganism belonging to the genus Bacillus. Any microorganism of this genus may be used so long as it has the ability to produce the thermophilic aspartase. Particularly preferred strains are *Bacillus licheniformis* T-514, *Bacillus brevis* T-616, *Bacillus aminogenes* nov. sp. T-596, and *Bacillus thermoaminophilus* nov. sp. T-585 which have been isolated and developed as biologically pure cultures by the inventors herein. More particularly, the T-514 strain was isolated from a factory drain in Yokkaichi-shi, Mie-ken, Japan; the T-616 and T-585 strains were isolated from the soil of the Beppu Spa in Beppu-shi, Oita-ken, Japan; and the T-596 strain was isolated from the soil of the Ibusuki Spa in Ibusuki-shi, kagoshima-ken, Japan.

These strains are characterized by the properties shown in Table 1.

TABLE 1

|  | T-514 | T-616 | T-596 | T-585 |
|---|---|---|---|---|
| I. Microscopic appearance | | | | |
| (1) Form and arrangement | $0.6-0.8 \times 2-4\mu$ Rods occasionally in chains | $0.8-1.0 \times 2-5\mu$ Rods occasionally in chains | $0.8-1.0 \times 2-5\mu$ Rods occasionally in chains | $0.6-0.8 \times 2-5\mu$ Rods occasionally in chains |
| (2) Gram stain | + | + | + | + |
| (3) Motility | + | + | + | + |
| (4) Endospore | | | | |
| Shape | Elliptical | Elliptical | Elliptical | Elliptical |
| Position | Central or terminal | Central or terminal | Central or terminal | Central or terminal |
| Swelling of sporangia | − | + | + | + |
| (5) Acid-fast stain | − | − | − | − |
| II. Culture characteristics | | | | |
| (1) Agar plate culture | | | | |
| Shape | Circular | Circular | Circular | Circular |
| Size (after 3 days) | 5–10 mm | 5–10 mm | 5–10 mm | 10–20 mm |
| Surface | Smooth | Smooth | Smooth | Smooth |
| Elevation | Raised | Raised | Raised | Raised |
| Edge | Undulate | Undulate | Undulate | Undulate |
| Content | Amorphous | Amorphous | Amorphous | Amorphous |
| Consistency | Butyrous | Butyrous | Butyrous | Butyrous |
| Color | Light yellowish brown to light violet brown | Light yellowish brown to brownish white | Light yellowish brown to brownish white | Brownish white to light yellowish brown |
| Density | Opaque | Opaque | Opaque | Opaque |
| Luster | Glistening | Glistening | Glistening | Glistening |
| (2) Agar slant culture | | | | |
| Growth | Good | Good | Good | Good |
| Form | Spreading to filiform | Spreading to filiform | Spreading to filiform | Spreading to plumose |
| (3) Liquid culture | | | | |
| Surface growth | Membranous | None | Membranous | None |
| Turbidity | Slight | Strong | Slight | Strong |
| Sediment | Viscid | Flocculent | Flocculent | Flocculent |
| (4) Stab culture | | | | |

TABLE 1-continued

|  | T-514 | T-616 | T-596 | T-585 |
|---|---|---|---|---|
| Growth | Good on surface | Good on surface | Good on surface | Good on surface |
| Form | Filiform | Filiform | Filiform | Filiform |
| III. Physiological properties | | | | |
| (1) Temperature range for growth (°C.) | 15–55 | 20–55 | 20–55 | 40–70 |
| (2) Optimum temperature for growth (°C.) | 40–50 | 40–50 | 40–50 | 55–60 |
| (3) pH range for growth | 5.5–9.0 | 5.0–9.0 | 5.0–9.0 | 5.0–8.0 |
| (4) Optimum pH for growth | 6.5–7.0 | 6.0–6.5 | 6.0–6.5 | 6.0–6.5 |
| (5) Requirement for oxygen | Facultative anaerobic | Aerobic | Aerobic | Aerobic |
| (6) Liquefaction of gelatin | + | + | − | + |
| (7) Action on litmus milk | Acidic peptonization | Acidic | No change | Acid formation (coagulation) |
| (8) Reduction of nitrate | + | − | − | − |
| (9) Denitrification | + | − | − | − |
| (10) Voges-Proskauer test | + | − | − | − |
| (11) pH in Voges-Proskauer broth | 5.6 | 8.5 | 8.3 | 8.6 |
| (12) Hydrolysis of starch | + | − | − | − |
| (13) Production of indole | − | − | − | − |
| (14) Production of hydrogen sulfide | − | + | − | + |
| (15) Urease | − | − | − | − |
| (16) Catalase | + | + | + | + |
| (17) Acid production from sugar | | | | |
| Glucose | + | + | + | + |
| Arabinose | − | − | − | − |
| Xylose | + | − | ± | − |
| Mannitol | + | + | ± | − |
| Fructose | + | + | + | − |
| Mannose | + | − | − | − |
| Galactose | − | − | − | − |
| Maltose | + | + | − | − |
| Sucrose | + | + | + | − |
| Trehalose | + | + | + | − |
| Glycerol | − | + | + | + |
| Sorbitol | − | − | − | − |
| (18) Gas formation from glucose | − | − | − | − |
| (19) Utilization of citric acid | + | + | + | − |
| (20) Utilization of propionic acid | + | + | + | + |
| (21) Utilization of acetic acid | + | ± | + | ± |
| (22) Utilization of fumaric acid | + | + | + | + |
| (23) Resistance to 7% sodium chloride | + | − | − | − |
| (24) Resistance to 0.02% azide | + | − | − | + |
| (25) Resistance to 0.001% lysozyme | + | + | ± | − |
| (26) Resistance to 0.1 μg/ml penicillin | + | − | + | − |
| (27) Decomposition of tyrosine | − | + | − | + |
| (28) Decomposition of casein | + | + | ± | + |
| (29) Deamination of phenylalanine | − | − | − | − |
| (30) Growth on Sabouraud dextrose medium | + | − | − | − |

The taxonomy of these strains was compared with reference to the descriptions in Bergey's Manual of Determinative Bacteriology, 8th edition (1974) and The Genus Bacillus by R. E. Gordon (Agricultural Research Service, U.S. Department of Agriculture) (1973). The strains are classified as belonging to the genus Bacillus from various characteristics. That is, they are rod-shaped, Gram-positive strains which form spores and grow under aerobic condition.

The properties of the T-514 strain are almost the same as those of the standard strain of *Bacillus licheniformis* used in comparative tests as the control strain and those of the *Bacillus licheniformis* strain described in the Bergey's Manual. Accordingly, the T-514 strain is classified as belonging to the species *Bacillus licheniformis*. The properties of the T-616 strain are almost the same as those of the standard strain of *Bacillus brevis* used in comparative tests as the control strain and those of the *Bacillus brevis* strain described in the Bergey's Manual. Accordingly, this strain is classified as belonging to the species *Bacillus brevis*.

The T-596 strain resembles *Bacillus brevis* in properties such as maximum temperature for growth, swelling of sporangia, growth under anaerobic condition, VP test, hydrolysis of starch, resistance to 7% sodium chloride, etc. However, the properties of the T-596 strain indicated in Table 2 are different from those of *Bacillus brevis* ATCC 8185. Moreover, the T-596 strain exhibits strong aspartase activity.

On the basis of these differences, the T-596 strain is regarded as a new species and is named *Bacillus aminogenes* nov. sp.

TABLE 2

| Properties | T-596 | ATCC 8185 | B. brevis* |
|---|---|---|---|
| Liquefaction of gelatin | − | + | |
| Reduction of nitrate | − | + | d |
| Production of hydrogen sulfide | − | + | |
| Utilization of acetic acid | + | − | |
| Utilization of fumaric acid | + | − | |
| Resistance to penicillin | + | − | |
| Decomposition of tyrosine | − | + | + |
| Growth on Sabouraud dextrose | − | + | d | d: The result is different by strains.
*Description in Bergey's Manual, 8th Ed.

The T-585 strain resembles *Bacillus stearothermophilus* in properties such as temperature range for growth, swelling of sporangia, growth under anaerobic conditions, VP test, resistance to 7% sodium chloride, etc. However, the properties of the strain, as indicated in Table 3, are different from those of *Bacillus stearothermophilus* ATCC 12980. Moreover, the T-585 strain exhibits strong aspartase activity. On the basis of these differences, the T-585 strain is regarded as a new species and is named *Bacillus thermoaminophilus* nov. sp.

TABLE 3

| Properties | T-585 | ATCC 12980 | B. stearothermophilus* |
|---|---|---|---|
| Liquefaction of gelatin | + | − | |
| Reduction of nitrate | − | + | d |
| Reaction of denitrogen | − | + | |
| pH on VP medium | 8.6 | 5.6 | 5.2–7.0 |
| Hydrolysis of starch | − | + | + |
| Production of hydrogen sulfide | + | − | |
| Production of acid from fructose, mannose, maltose & trehalose | − | + | |
| Utilization of tyrosine | + | − | − |
| Resistance to azide | + | − | − | d: The result is different by strains
*Description in Bergey's Manual, 8th Ed.

The T-585, T-596, T-514 and T-616 strains have been deposited with the Culture Collection Research Fermentation Laboratory, Northern Regional Research Center, Peoria, Ill. 61604 and are available to the public under culture Nos. NRRL B-12060, B-12061, B-12062 and B-12063 respectively.

The strains have also been deposited with the Fermentation Research Institute, Japan and assigned the registered numbers FERM-P Nos. 5239, 5240, 5241 and 5242 respectively.

In a biologically pure culture, each of the foregoing strains is characterized by the ability to produce thermophilic aspartase in recoverable quantities.

As is the case with other strains belonging to the genus Bacillus, the microorganism useful in carrying out the present invention can be mutated by artificial means such as ultraviolet irradiation, $Co^{60}$ irradiation, X-ray irradiation and the action of various mutagens such as N-methyl-N'-nitro-N-nitrosoguanidine, etc. Accordingly, any strain even if thus mutated, is contemplated as appropriate for the present invention insofar as it has the ability to produce thermophilic aspartase as characterized hereinafter.

Generally, conventional methods for culturing bacteria may be employed in the process of the present invention.

Appropriate carbon sources include carbohydrates such as glucose, fructose, maltose, sucrose, mannitol starch, molasses, glycerin, etc. either alone or in combination. Hydrocarbons, alcohols, organic acids etc. may be used depending upon the assimilability possessed by the microorganisms used.

As nitrogen sources, inorganic nitrogen-containing compounds such as ammonium sulfate, ammonium chloride, ammonium nitrate, sodium nitrate, urea and the like, organic nitrogen-containing compounds such as polypepton, peptone, yeast extract, corn steep liquor, amino acids, meat extract, soybean powder, casamino acid, soluble vegetable protein, etc. may be used either alone or in combination.

If necessary, inorganic salts such as sodium chloride, potassium chloride, magnesium sulfate, calcium carbonate, potassium dihydrogen phosphate, dipotassium hydrogen phosphate, ferrous sulfate, calcium chloride, manganese sulfate, zinc sulfate, copper sulfate, etc. may be added to the medium.

Moreover, organic and inorganic materials such as fumaric acid, malic acid, pyruvic acid, various vitamins, etc. which promote the growth of the particular strain and enhance the production of the enzyme may be added to the medium.

A liquid culturing method, particularly a submerged stirring culturing method is most suitable. Culturing is carried out at a temperature of 30°–60° C. and at a pH of 5–8, preferably 6–7.5 until substantial enzymatic activity is detectable.

After completion of culturing, the purification and isolation of the enzyme are carried out by conventional methods for the isolation and purification of enzymes from a culture liquor. For example, the culture liquor is centrifuged to obtain microbial cells. The cells are washed thoroughly with water and are disrupted in a buffer at a concentration of about 50 g/l to obtain a cell-free extract. Streptomycin sulfate or protamine sulfate is added to the extract to a concentration of 5–30 mg/ml to remove nuclei. Then the pH of the mixture is adjusted to about 5.0 with 0.1 M acetic acid. The mixture is centrifuged to obtain a supernatant which is adjusted to pH 7.0 with potassium hydroxide.

The solution is then subjected to salting-out using 0–30%, 30–55%, 55–75% ammonium sulfate and the resultant precipitate is subjected to column chromatography using DEAE-cellulose, Sephadex G-100 or the like. The resulting solution is extracted with ammonium sulfate and the extract is freeze-dried to obtain an enzyme preparate.

Enzyme activity is determined by the following method.

An enzyme preparate, microbial cells or treated matter of the culture liquor are incubated in the presence of 0.1 M ammonium fumarate at a temperature of 35°–60° C. and at a pH of 8.0 for 30 minutes. The treated matter of the culture liquor, as used herein, means the substances exhibiting aspartase activity obtained in the course of purification and isolation processes of the enzyme from the culture liquor. The reaction solution is diluted with water so that the concentration of fumaric acid is in the range of 1–10 g/l. The solution is titrated with potassium permanganate under acidic condition with sulfuric acid. The aspartase activity is determined from the amount of fumaric acid remaining in the reaction solution.

As other methods for the determination of the activity, a high performance liquid chromatography method using Shodex OH Pak column and a Warburg method using L-aspartic acid-4-decarboxylase may be applied. In any case, the enzyme activity is indicated by the international unit (unit/g.cell).

The properties of the thermophilic aspartase of the invention are illustrated below.

(1) Action

The enzyme acts only on fumarate and L-aspartate and catalyzes the conversion of fumaric acid and ammonia to L-aspartic acid.

(2) Optimum pH

Enzyme activity is determined in 0.1 M phosphate buffer (pH 7.0–8.0) or 0.1 M Tris-hydrochloride buffer (8.0–9.5) in the presence of 15 g/l ammonium fumarate as a substrate at 55° C. for one hour. The results are shown in FIG. 1. The optimum pH is about 8.5–9.0.

(3) pH stability

Figure 2:
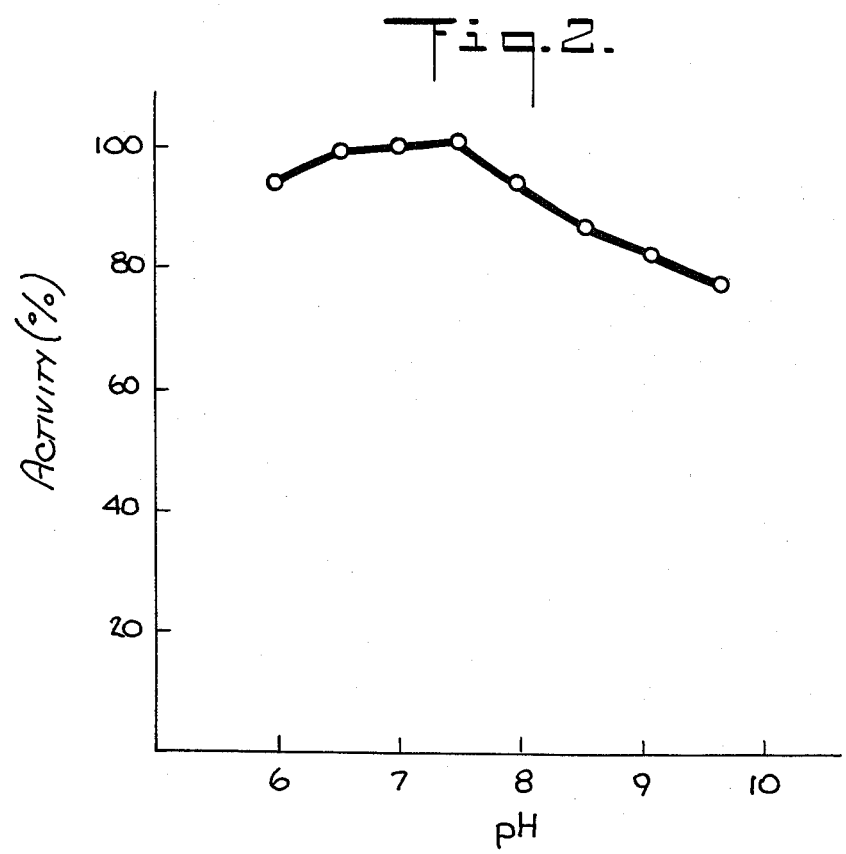

The enzyme is incubated in 0.2 M phosphate buffer (pH 6.0–8.0) or 0.2 M Tris-hydrochloride buffer (pH 7.5–9.5) at various pH values and at 50° C. for 17 hours. The mixture is subjected to reaction at a pH of 8.5 for 30 minutes, and the enzyme activity of the reaction solution is determined. The results are shown in FIG. 2. The enzyme is stable in the pH range of 7.0–8.5.

(4) Optimum temperature

Figure 3:
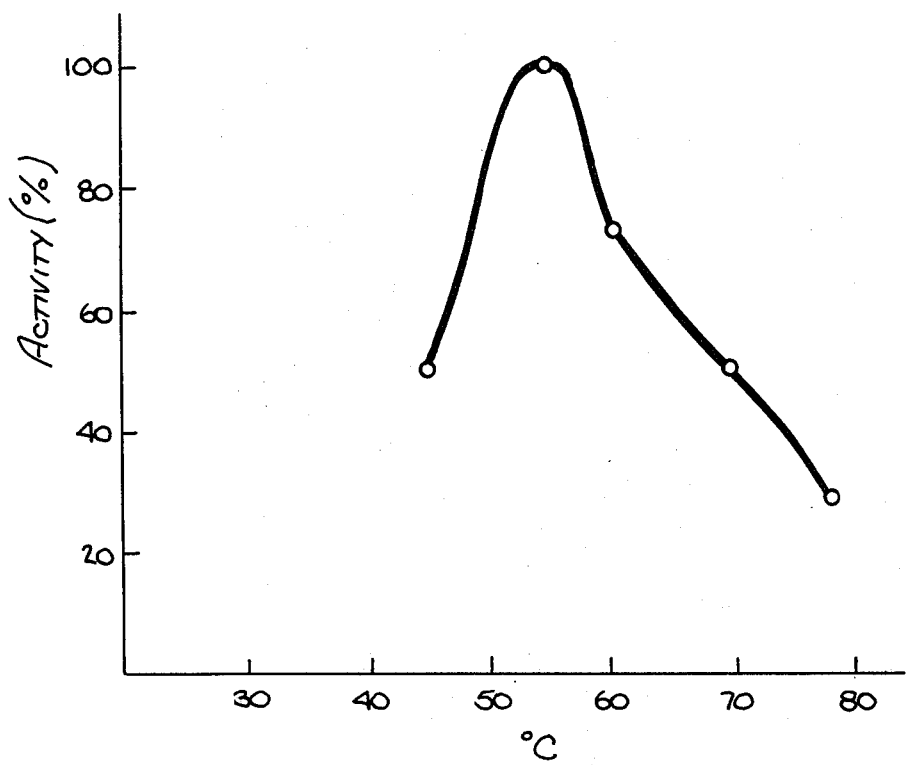

The enzyme is incubated at 45°–80° C. and at a pH of 8.0 for 30 minutes. The results are shown in FIG. 3. The optimum temperature is about 55° C.

(5) Thermo stability

Figure 4:
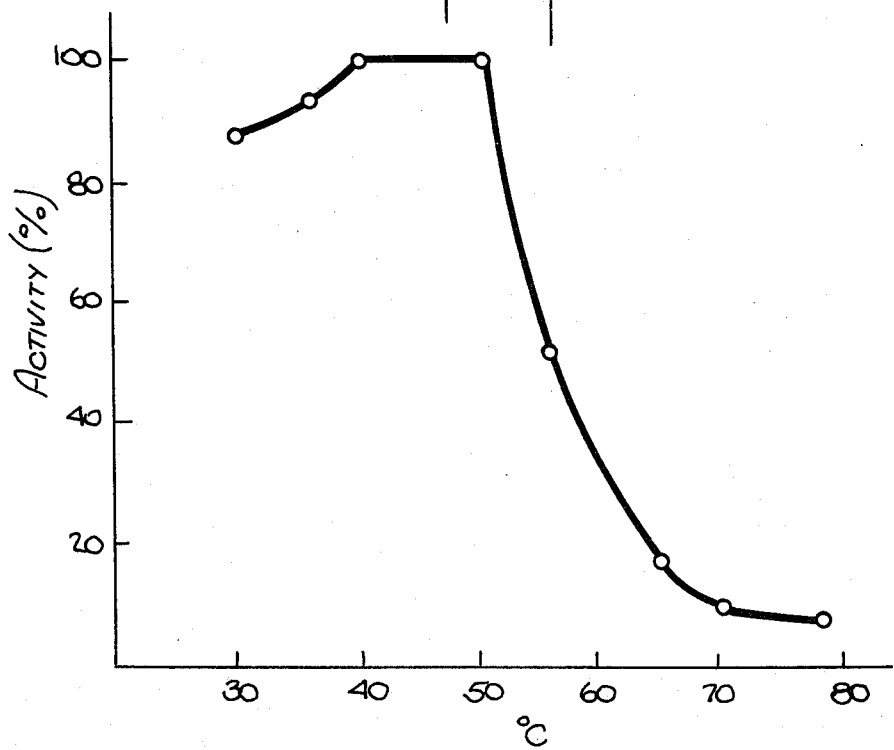

The enzyme is incubated in 0.1 M phosphate buffer (pH 7.0) at 30°–80° C. for 60 minutes. To the solution is added ammonium fumarate to make a concentration of 100 g/l and the reaction is carried out at 50° C. for 30 minutes. The results are shown in FIG. 4. The enzyme is stable at a temperature of less than 50° C.

(6) Activation and stabilization

The enzyme is stabilized in the presence of ammonium fumarate and L-aspartic acid. The enzyme is activated in the presence of divalent metal ions such as $Mg^{++}$, $Mo^{++}$, $Co^{++}$ and $Zn^{++}$.

(7) Molecular weight

The enzyme is subjected to gel filtration using Sephadex G-200 and using cytochrome C, ovalbumin, and γ-globulin as an internal standard protein to give a molecular weight of about 175,000.

Ammonium fumarate or a mixture of fumaric acid and ammonia is converted to L-aspartic acid by the action of the enzyme, cells or treated matter of the culture liquor. The enzymatic reaction is carried out at 35°–60° C. and at a pH of 7.0–8.5. The preferred concentration of reactants is 0.2–2.0 mol/l. The enzyme is used in a concentration of 1–10 unit/ml.

L-aspartic acid is efficiently produced by using an immobilized enzyme, cells, or treated matter of the culture liquor. Immobilization is performed according to the methods usually used for immobilizing enzymes, cells or treated matter of the culture liquor. For example, the enzyme may be used by adsorbing it on an anion exchange resin capable of adsorbing the enzyme. In the immobilization of cells, microencapsulating methods using ethyl cellulose, cellulose acetate butyrate and the like, gel entrapping methods using a monomer of acryl amide and polyvinylalcohol and membrane entrapping methods using collagen, etc. are applicable.

A method wherein the cells are mixed with a packing agent and then treated with a cross-linking agent may also be used. Examples of suitable packing agents are gelatin, chitosan, carrageenan and albumin. The cross-linking agent includes glutaraldehyde and dialdehyde starch.

The recovery of L-aspartic acid from the reaction solution is carried out by adjusting the pH of the solution to the isoelectric point, pH 2.77 with sulfuric acid and aging the solution under cooling to obtain crystals of L-aspartic acid. To elevate the purity of the compound, the crystals are reslurried to a concentration of 300 g/l and then the mixture is aged under cooling.

Certain specific embodiments of the invention are illustrated by the following representative examples.

EXAMPLE 1

In this example, *Bacillus aminogenes* T-596, *Bacillus brevis* T-616, *Bacillus thermoaminophilus* T-585 and *Bacillus licheniformis* T-514 are inoculated in 30 ml of a medium (pH 7.0) containing 8 g/l polypepton, 4 g/l yeast extract and 2 g/l sodium chloride in a 300 ml-flask and are cultured at temperatures indicated in Table 4 for 18 hours. The seed cultures are then transferred to 300 ml of a medium (pH 7.2) containing 30 g/l glucose, 25 g/l peptone, 4 g/l meat extract, 5 g/l calcium carbonate and 1 ml/l soybean oil in a 2 l-flask provided with baffles and are cultured at temperatures indicated in Table 4 for 24 hours to obtain microbial cells in the amounts indicated in Table 4. The culture liquors are subjected to centrifugation at 8000 G and the resultant cells are washed with 0.01 M phosphate buffer (pH 7.2). The wet cells are suspended in 1 mole of ammonium fumarate in a cell concentration of 10 g/l and incubated at an optimum temperature of the microorganism for 30 minutes. The aspartase activity is determined from the amount of L-aspartic acid produced. The results are shown in Table 4.

TABLE 4

| Microorganism | Temperature [°C.] | OD value* | Aspartase activity [unit/g · cell] |
|---|---|---|---|
| T-596 | 50 | 0.072 | 2,000 |
| T-585 | 60 | 0.200 | 400 |
| T-616 | 40 | 0.080 | 80 |
| T-514 | 50 | 0.092 | 110 |

*Optical density of the culture liquor diluted twenty times at 660 nm.

EXAMPLE 2

In this example, *Bacillus aminogenes* T-596 is seed cultured as in Example 1. The seed culture is inoculated into a medium containing 20 g/l glucose, 10 g/l ammonium fumarate, 25 g/l peptone, 4 g/l meat extract, 0.25 g/l magnesium sulfate, 0.25 g/l sodium molibudenate, 1.4 g/l clacium chloride and 1.2 ml/l soybean oil in a 30 l-jar fermenter. Culturing is carried out at a temperature of 46° C. with stirring of 200 r.p.m. and with aeration of 0.8 v.v.m. for 17.5 hours to obtain 9.0 g/l of microbial cells having aspartase activity of 2000 unit/g dry.cell. The culture liquor is subjected to centrifugation with a tubular centrifuge at 12,000 G and the resultant cells are washed twice with 0.01 M phosphate buffer (pH 8.0).

Then the cells are freeze-dried to obtain a cell preparation.

EXAMPLE 3

In this example, 500 g of freeze-dried cells obtained in Example 2 is suspended in 10 l of 0.05 M phosphate buffer (pH 8.5) and the suspension is subjected to disruption with a disintegrater Dyno Mill. The resultant mixture is subjected to centrifugation at 8000 G to obtain a cell-freeze extract. Then, 6 l of the extract is charged on a column packed with 1.2 l of a weakly basic anion exchange resin, Duolite A7 (product of Diamond Shamrock Chemical Co., U.S.A.), at a flow rate of 15 l/hr, at room temperature to obtain resins on which about 20 mg of protein per ml resin is loaded. Thereafter, 3 l of 0.1 M phosphate buffer (pH 8.5) containing 20 g/l ammonium fumarate and 3 l of 0.4% glutaraldehyde are added to the resin and the mixture is subjected to cross-linking reaction for 30 minutes. The mixture is then washed with water to remove glutaraldehyde and to obtain the immobilized enzyme.

The thus obtained immobilized enzyme is charged into a 50 ml-column and 1 M ammonium fumarate (pH 8.5) is passed through the column with a space velocity of 1.0–1.1 at 50° C. L-aspartic acid is continuously produced for 20 days at a conversion ratio of 98% or more. The reaction solution is a complete supernatant and no enzyme is lost. Contamination does not occur owing to the high temperature during the enzymatic reaction for the production of the L-aspartic acid.

EXAMPLE 4

In this example, *Bacillus thermoaminophilus* T-585 is cultured in a medium having the same composition as in Example 1 at 60° C. for 24 hours.

After the culture liquor is centrifuged, the cells are washed thoroughly with water and are then freeze-dried to obtain dry cells having aspartase activity of 400 unit/g dry·cell.

The thus obtained cells are immobilized by first dissolving 0.72 g of Emulgen-985 (product of Kao Atras Co.) and 0.3 g of Celogen-PR (product of Daiichi Kogyo Pharmaceutic Co.) as the dispersing agent in 60 ml of water and vigorously stirring the solution at 5°–10° C. to obtain a disperse medium. Separately 1.5 g of the freeze-dried cells is homogeneously suspended in a mixed solution of 5 l of 0.9% saline and 1.5 ml of 1% chitosan. Then, 1.5 g of cellulose acetate butyrate 381-20 (product of Eastman Chemical International Co.) and 0.3 g of Alracel-83 (product of Kao Atras Co.) as the dispersing agent are dissolved in 13.5 g of isobutyl acetate and the solution is thoroughly stirred to obtain a homogeneous W/O emulsion. The cell suspension and the emulsion are added dropwise to the above disperse medium with stirring under cooling. Then, 120 ml of n-hexane is added quantitatively and little by little with a pump to deposit firm immobilized cells having a uniform size which are entrapped within the cellulose acetate butyrate. The immobilized cells are obtained by filtration and washed thoroughly. Then, 1 M ammonium fumarate is passed through a column packed with the immobilized cells with a space velocity of 1.0 at 50° C. L-aspartic acid is continuously produced for one week at a conversion ratio of 95% or more. The pH of the reaction mixture is then adjusted to 2.77 with sulfuric acid to form crystals of L-aspartic acid.

EXAMPLE 5

In this example, *Bacillus aminogenes* T-596 is cultured as in Example 2. The obtained cells are disrupted with an ultrasonic disintegrater in a concentration of 50 g/l. To the supernatant, 30 mg/ml protamine sulfate is added to form a precipitate and the precipitate is separated by centrifugation. Then, the pH of the supernatant is adjusted to 5.0 with 0.1 M acetic acid and the formed precipitate is separated by centrifugation. The pH of the supernatant is adjusted to 7.0 with potassium hydroxide.

Then the solution is subjected to concentration gradient salting-out with 0–30%, 30–55% and 55–75% ammonium sulfate. The thus obtained solution is subjected to chromatography using DEAE.cellulose. Active fractions are combined and ammonium sulfate is added to the solution to obtain a precipitate. The precipitate is freeze-dried to obtain an enzyme preparate in powder form.

The specific activity of the aspartase per protein is about 100 times that of the cell-free extract.

What is claimed is:

1. A process for producing thermophilic aspartase which comprises culturing a thermophilic aspartase producing *Bacillus aminogenes* having the identifying characterestics of NRRL B12061 or *Bacillus thermoaminophilus* having the identifying characteristics of NRRL B12060 in a nutrient medium until substantial enzymatic activity is detectable and thereafter isolating said thermophilic aspartase.

2. A process according to claim 1 wherein said culturing step is carried out at a temperature of 30° to 60° C. and at a pH of from 6 to 7.5.

3. A biologically pure culture of *Bacillus thermoaminophilus* having the identifying characteristics of NRRL B-12060, which produces thermophilic aspartase in recoverable quantities upon culturing.

4. A biologically pure culture of *Bacillus aminogenes* having the identifying characteristics of NRRL B-12061, which produces thermophilic aspartase in recoverable quantities upon culturing.

* * * * *